United States Patent [19]

Merger et al.

[11] Patent Number: 5,254,757
[45] Date of Patent: Oct. 19, 1993

[54] PREPARATION OF 2,2-BIS-HYDROXYMETHYL-BUTANEDIOL-(1,4)

[75] Inventors: Franz Merger, Frankenthal; Martin Schmidt-Radde, Ludwigshafen, both of Fed. Rep. of Germany

[73] Assignee: BASF Aktiengesellschaft, Ludwigshafen, Fed. Rep. of Germany

[21] Appl. No.: 964,865

[22] Filed: Oct. 22, 1993

[30] Foreign Application Priority Data

Oct. 22, 1991 [DE] Fed. Rep. of Germany ....... 4134771

[51] Int. Cl.$^5$ .................. C07C 27/04; C07C 29/145; C07C 31/18
[52] U.S. Cl. .................................. 568/863; 568/852
[58] Field of Search ................. 568/861, 862, 863, 852

[56]  References Cited
U.S. PATENT DOCUMENTS

| | | | |
|---|---|---|---|
| 3,235,515 | 2/1966 | Taylor | 252/472 |
| 3,449,445 | 6/1969 | Wetherill | 568/452 |
| 4,386,018 | 5/1983 | Merger et al. | 252/465 |
| 4,859,801 | 8/1992 | Ernst | 568/862 |
| 4,861,922 | 8/1989 | Tokitoh et al. | 568/862 |
| 4,950,797 | 8/1990 | Kummer et al. | 568/450 |
| 4,956,328 | 9/1990 | Fronning et al. | 502/328 |

FOREIGN PATENT DOCUMENTS

| | | |
|---|---|---|
| 044444 | 6/1981 | European Pat. Off. . |
| 335222 | 3/1984 | European Pat. Off. . |
| 150943 | 8/1985 | European Pat. Off. . |
| 293818 | 5/1988 | European Pat. Off. . |
| 340970 | 11/1989 | European Pat. Off. . |
| 1257753 | 8/1968 | Fed. Rep. of Germany . |
| 2321101 | 11/1974 | Fed. Rep. of Germany . |
| 3904083 | 8/1990 | Fed. Rep. of Germany . |

OTHER PUBLICATIONS

Preparation of 2,2-Bis(hydroxymethyl)-3-butent-1 ... Kuhn et al. Jul. 1959 Notes 1005-1006.
Catalytic Hydrogenation, Augustine, J. Catalysts and Conditioins pp. 25-56.

Primary Examiner—Werren B. Lone
Attorney, Agent, or Firm—Keil & Weinkauf

[57] ABSTRACT

A process for the preparation of 2,2-bis-hydroxymethyl-butanediol-(1,4) of formula I

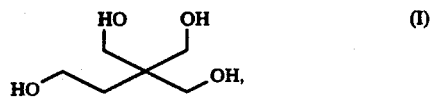

wherein 4-hydroxybutyraldehyde of formula II

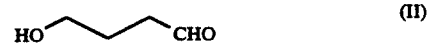

and/or 2-hydroxytetrahydrofuran of formula III

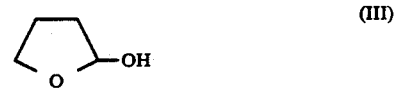

is/are condensed with formaldehyde in the presence of a basic catalyst and the resulting reaction mixture is then catalytically hydrogenated, and 2,2-bis-hydroxymethyl-butanediol-(1,4) is isolated from the hydrogenation product.

6 Claims, No Drawings

PREPARATION OF 2,2-BIS-HYDROXYMETHYL-BUTANEDIOL-(1,4)

The present invention relates to a process for the preparation of 2,2-bis-hydroxymethyl-butanediol-(1,4) of formula I

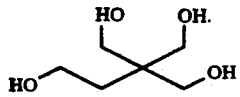
(I)

According to J. Org. Chem. 24, 1005 (1959), the co-aldolization of 4-hydroxybutyraldehyde with formaldehyde with batchwise hydrogenation of the resulting crude 2,2-bis-hydroxymethyl-butyraldehyde with Raney nickel yields a viscous syrup, from which 2,2-bis-hydroxymethyl-butanediol-(1,4) cannot be isolated by conventional separation techniques. To obtain compound I, it is necessary to acetylize the resulting hydrogenation mixture with acetic anhydride to form the tetraacetic acid ester, which can be isolated and converted to compound I by transesterification with methanol. Using this method, it is only possible to synthesize 2,2-bis-hydroxymethyl-butanediol-(1,4) (I), referred to below as BHB, in an overall yield of 24%, based on 4-hydroxybutyraldehyde. This highly unsatisfactory yield and the very laborious and costly method used for the isolation of the target product makes this process unsuitable for industrial applications.

The low yields are possibly due to side reactions occurring between the intermediate products 4-hydroxy-2-hydroxymethyl-butyraldehyde and 2,2-bis-hydroxymethyl-butyraldehyde, such as dehydrations, retro-aldolizations, and polymerizations, but such a possibility has not been subjected to close examination.

EP-A 340,970 reveals that the reaction of 4-hydroxybutyraldehyde with formaldehyde under hydrogenating conditions produces virtually only 2-methyl-butanediol-(1,4) and 1,4-butanediol. BHB is apparently not formed under these conditions.

It is thus an object of the invention to provide a process for the economical preparation of BHB.

Accordingly, we have found a process for the preparation of 2,2-bis-hydroxymethyl-butanediol-(1,4) of formula I

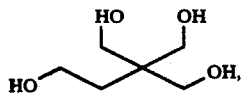
(I)

wherein 4-hydroxybutyraldehyde of formula II

(II)

and/or 2-hydroxytetrahydrofuran of formula III

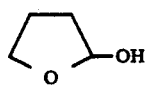
(III)

is/are condensed with formaldehyde in the presence of a basic catalyst and the resulting reaction mixture is then catalytically hydrogenated, and 2,2-bis-hydroxymethyl-butanediol-(1,4) is isolated from the hydrogenation product.

The chemical reactions forming the basis of the process of the invention are illustrated by the following reaction schemes:

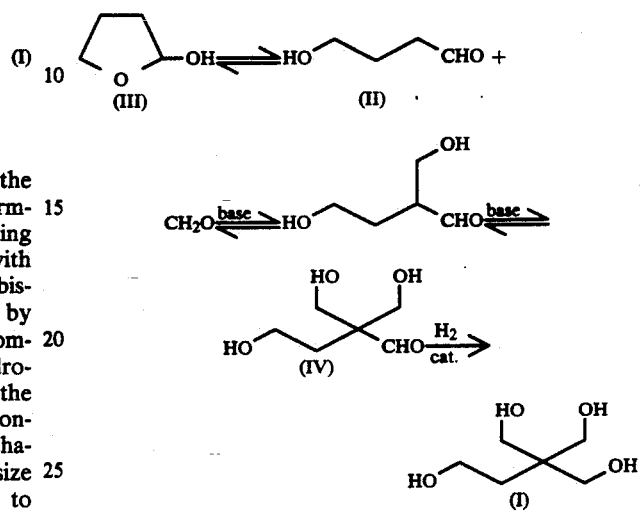

4-Hydroxybutyraldehyde II, in equilibrium with its cyclic half-acetal 2-hydroxytetrahydrofuran III, is condensed in an aldolization with 2 molecules of formaldehyde to form 2,2-bis-hydroxymethyl-butyraldehyde IV, which is then hydrogenated to BHB.

To effect the aldolization, the formaldehyde is reacted with the 4-hydroxybutyraldehyde II generally in a molar ratio of from 1.5:1 to 3.0:1 and preferably from 1.8:1 to 2.5:1. The formaldehyde is advantageously used in the form of an aqueous solution, in which the concentration of formaldehyde can be, advantageously, from 10 to 50 wt %.

Suitable basic catalysts for use in the aldolization of the formaldehyde with 4-hydroxbutyraldehyde are, basically, all of such bases as are commonly used for catalyzing aldol condensations, for example the hydroxides and carbonates of alkali metals and alkaline earth metals, tertiary amines and basic ion exchangers, but in the process of the invention particular preference is given to tertiary amines, especially tertiary alkylamines.

The tertiary amines used as catalysts in the process of the invention may be aliphatic, cycloaliphatic, or heterocycloaliphatic tertiary amines. It is advantageous to use tertiary amines which contain from 3 to 20 carbon atoms and preferably from 3 to 15 carbon atoms. Particularly preferred tertiary amines are those which are made up of $C_1$–$C_4$ alkyl groups. The following tertiary amines are mentioned by way of example: trimethylamine, triethylamine, tri-n-propylamine, tri-n-butylamine, triisopropylamine, triisobutylamine, methyldiethylamine, methyldiisopropylamine, ethyldiisopropylamine, dimethyl-tert-butylamine, N,N'-tetramethyl-ethylenediamine, N,N',N"-pentamethyl-ethylenetriamine, cyclohexyl-dimethylamine, dicyclohexylmethylamine, tribenzylamine, benzyldimethylamine, N-methylpyrrolidine, N-methylpiperidine, N,N'-dimethylpiperazine, N,N'-diethylpiperazine, N-methylmorpholine, triethanolamine, methyldiethanolamine, quinuclidine, and 1,4-diazabicyclo[2.2.2]octane.

The base is usually used in a concentration of from 0.5 to 25 mol % and preferably from 1.0 to 10 mol %, based on the 4-hydroxybutyraldehyde.

The condensation of the 4-hydroxybutyraldehyde with formaldehyde is generally carried out at a temperature of from 0° to 100° C. and preferably from 1° to 70° C. and more preferably from 1° to 40° C. The reaction is advantageously carried out at atmospheric pressure. It is also possible to operate under pressure, preferably the autogenous pressure of the reaction system, or under reduced pressure.

The aldol condensation is normally carried out in an aqueous reaction medium, but there may be added, if desired, other, organic solvents which are inert under the reaction conditions and which are preferably readily miscible with water, such as tetrahydrofuran, dioxane, and dimethoxyethane.

On completion of the aldol condensation and prior to the hydrogenation, the basic catalyst may, if desired, be neutralized by the addition of an acid, and it is preferred that neutralization be effected by the use of an acidic ion exchanger, which can be easily removed from the reaction mixture by mechanical separation, e.g., filtration or centrifugation. This technique is particularly useful when inorganic catalysts are used. If distillable basic catalysts, such as tertiary amines, are used for the aldol condensation, they can be removed from the reaction mixture, if desired, by distillation. Alternatively, the following hydrogenation stage can be carried out in the presence of such basic catalysts. In particular, in the preferred embodiment of the process of the invention, i.e., when a tertiary amine is used as the aldol condensation catalyst, the hydrogenation of the aldolization product may be carried out in situ, i.e., without previously separating the catalyst.

For the hydrogenation, the 2,2-is-hydroxymethyl-butyraldehyde IV is advantageously used in a solution having a content of IV of not more than 50 wt %. Prior to the hydrogenation, it is therefore advantageous to add a further quantity of solvent to the reaction mixture coming from the aldol condensation. It is particularly preferred to dilute said reaction mixture with water such that the solution to be hydrogenated has a water content of, usually, from 50 to 90 wt % and preferably from 70 to 85 wt %.

Alternatively, an organic solvent may be added to the reaction mixture coming from the aldol condensation instead of water, which solvent must be inert under the conditions of hydrogenation and is preferably one which is readily miscible with the water already present in the reaction mixture.

Examples of suitable solvents are ethers such as tetrahydrofuran, dioxane, and dimethoxyethane, $C_1$-$C_4$ alcohols, in particular methanol, ethanol, propanol, and isopropanol, ethylene glycol, methoxyethanol, and ethoxyethanol.

A further possibility is to remove all or some of the water from the reaction mixture to be hydrogenated, for example by distillation, and then to replace it completely or partially by an organic solvent. If all or most of the water is removed from the reaction mixture, it can be replaced by an organic solvent which is immiscible or less readily miscible with water. In the case of the use or co-use of organic solvent, it is advantageous to add this to the reaction mixture to be hydrogenated in such quantity that the total concentration of water and/or organic solvent in the reaction mixture to be hydrogenated is from 50 to 90 wt % and preferably from 70 to 85 wt %.

The hydrogenation of the resulting solution containing the aldol condensation product, 2,2-bis-hydroxymethyl-4-hydroxybutyraldehyde, can be carried out in conventional manner at temperatures generally ranging from 70° to 200° C. and under a pressure of, usually, from 1 to 200 bar. Hydrogenation is preferably carried out using a heterogeneous catalyst. This hydrogenation catalyst can be suspended in the reaction mixture or take the form of a fixed bed. The mixture to be hydrogenated can be passed upwardly through the fixed bed or allowed to trickle downwardly through the fixed bed. The residence times used are generally from 10 to 300 min and preferably from 20 to 120 min.

To effect hydrogenation of 2,2-bis-hydroxymethyl-4-hydroxybutyraldehyde to BHB it is possible to use basically any of the conventional hydrogenation catalysts, for example catalysts containing nickel, cobalt, copper, manganese, molybdenum, rhenium and/or the platinum metals palladium, platinum, and ruthenium. It is possible to use the pure metals, finely divided or in the form of nets or other structures of large surface area, or catalysts containing a plurality of these metals. The hydrogenation catalysts may be used in the form of solid catalysts or supported catalysts. In the latter case conventional support materials may be used, for example silicon dioxide, aluminum oxides, zirconium dioxide, titanium dioxides, activated charcoal, barium sulfate, barium carbonate, calcium carbonate and the like. Reference is made, by way of example, to the hydrogenation catalysts taught in R. L. Augustine, *Catalytic Hydrogenation*, Chapter 3, Marcel Dekker, Inc., New York 1965, EP-A 335,222, DE-A 1,257,753, U.S. Pat. No. 3,449,445, DE-A 2,321,101, EP-A 44,444, and DE-A 3,904,083. It is preferred to use, in the process of the invention, catalysts containing copper and/or cobalt and/or ruthenium catalysts, especially ruthenium on alumina. Particularly preferred copper- and/or cobalt-containing catalysts are the catalysts disclosed in DE-A 2,321,101, EP-A 44,444, and DE-A 3,904,083.

Both the aldol condensation and the hydrogenation can be carried out batchwise or continuously in conventional reactors.

The desired product BHB can be isolated from the hydrogenation mixture in a simple manner by conventional methods, for example by the extraction of an aqueous hydrogenation solution by means of an organic solvent which is sparingly soluble in water, examples being sparingly soluble alcohols, ketones, ethers, esters, and halogenated hydrocarbons, or by crystallization. The BHB is preferably purified and isolated by distillation. During distillation, the tertiary amine which may have been used as catalyst can be recovered and, if desired, recycled to the aldol condensation stage.

The target product BHB is produced by the process of the invention economically and in good yields and high purity.

BHB has many applications. For example it can be used in the manufacture of alkyd resins and coatings, as the polyol component in the manufacture of polyurethanes, and in the manufacture of plasticizers and emulsifiers.

The 4-hydroxybutyraldehyde used for the synthesis thereof can be obtained as proposed in EP-A 293,818 by isomerization of 2-butenediol-(1,4) or alternatively via the hydroformylation of allyl alcohol, as described in EP-A 150,943.

EXAMPLES

Example 1

176 g (2 mol) of 4-hydroxybutyraldehyde, 500 g of 30 wt % formalin (5 mol of formaldehyde) and 3 g (0.03 mol) of triethylamine were mixed together and stirred for 1 h at 25° C. and then for 1 h at 40° C. The reaction mixture was then diluted with 1000 g of water, and the resulting solution was continuously hydrogenated at a temperature of 130° C. and a pressure of 90 bar. The hydrogenation catalyst used was a copper on alumina catalyst as described in EP-A 44,444, in which the copper content (calculated as CuO) was 55 wt % and the alumina content (calculated as $Al_2O_3$) was 44.5 wt %. The throughput was 1.2 L of solution per liter of catalyst per hour. The hydrogenation product was worked up by distillation to give 201 g of BHB (bp 200°–205° C./1 torr; mp 87°–88° C.) corresponding to a yield of 67% based on 4-hydroxybutyraldehyde used.

Example 2

The aldol condensation was carried out as described in Example 1. Substantially all of the water present in the reaction mixture was then distilled off under reduced pressure (3 mbar, temperature at bottom of still: 50° C.), and the residues were dissolved in three times their weight of tetrahydrofuran. The resulting solution was continuously hydrogenated at a temperature of 170° C. and a pressure of 90 bar. The hydrogenation catalyst used was a catalyst as described in DE-A 3,904,083 and containing 66.8 wt % of cobalt (calculated as CoO), 19.1 wt % of copper (calculated as CuO), 7.1 wt % of manganese (calculated as $Mn_2O_3$), 3.3 wt % of molybdenum (calculated as $MoO_3$), 3.5 wt % of phosphoric acid (calculated as $H_3PO_4$), and 0.15 wt % of sodium (calculated as $Na_2O$). The throughput through the catalyst was 1.9 L/(L·h). Following purification of the hydrogenation product by distillation, BHB was obtained in a total yield of 54% based on 4-hydroxybutyraldehyde used.

We claim:

1. A process for the preparation of 2,2-bis-hydroxymethyl-butanediol-(1,4) of formula I

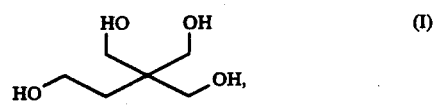

which comprises: condensing 4-hydroxybutyraldehyde of formula II

and/or 2-hydroxytetrahydrofuran of formula III

with formaldehyde in the presence of a basic catalyst at a temperature of from 0° to 100° C. catalytically hydrogenating the resulting reaction mixture at a temperature of from 70° to 200° C. and a pressure of from 1 to 200 bar and isolating 2,2-bis-hydroxymethyl-butanediol-(1,4) from the hydrogenation product.

2. The process of claim 1, wherein the basic catalyst used is a tertiary amine.

3. The process of claim 1, wherein the hydrogenation is carried out in an organic solvent or a mixture of organic solvent and water.

4. The process of claim 1, wherein the reaction mixture to be hydrogenated has a water content of from 50 to 90 wt %.

5. The process of claim 1, wherein the hydrogenation is carried out over a heterogeneous hydrogenation catalyst in the presence of hydrogen.

6. The process of claim 1, wherein the condensation reaction takes place at a temperature of from 1° to 70° C.

* * * * *